(12) United States Patent
Kumagai et al.

(10) Patent No.: US 9,816,921 B2
(45) Date of Patent: Nov. 14, 2017

(54) MATERIAL ANALYTICAL SENSOR AND MATERIAL ANALYZER (71) Applicant: Kabushiki Kaisha TOPCON, Tokyo (JP)

(72) Inventors: Kaoru Kumagai, Tokyo (JP); Shugo Akiyama, Tokyo (JP)

(73) Assignee: Kabushiki Kaisha TOPCON, Tokyo (JP)

( * ) Notice: Subject to any disclaimer, the term of this patent is extended or adjusted under 35 U.S.C. 154(b) by 77 days.

(21) Appl. No.: 14/969,970

(22) Filed: Dec. 15, 2015

(65) Prior Publication Data
US 2016/0169795 A1 Jun. 16, 2016

(30) Foreign Application Priority Data

Dec. 16, 2014 (JP) .................. 2014-253795

(51) Int. Cl.
*G01N 21/35* (2014.01)
*G01N 21/31* (2006.01)
(Continued)

(52) U.S. Cl.
CPC .......... *G01N 21/359* (2013.01); *G01J 3/0232* (2013.01); *G01J 3/10* (2013.01);
(Continued)

(58) Field of Classification Search
CPC .. G01J 3/0232; G01J 3/10; G01J 3/42; G01N 2021/3148; G01N 2021/3155;
(Continued)

(56) References Cited

U.S. PATENT DOCUMENTS 5,220,168 A 6/1993 Adamski et al.
5,258,825 A 11/1993 Reed et al.
(Continued)

FOREIGN PATENT DOCUMENTS

| EP | 2 158 801 A1 | 3/2010 |
| EP | 2 526 754 A1 | 11/2012 |
| WO | WO 03/026383 A1 | 4/2003 |

OTHER PUBLICATIONS

Curcio J A, et al: "The Near Infrared Absorption Spectrum of Liquid Water", Journal of the Optical Society of America, American Institute of Physics, New York; US, vol. 41, (1951); pp. 302-304.
(Continued)

*Primary Examiner* — Mark R Gaworecki
(74) *Attorney, Agent, or Firm* — Blank Rome LLP (57) ABSTRACT

A material analytical sensor includes an emitter that irradiates a material with irradiation light including a wavelength region related to estimation of an amount of a component of the material, a controller that controls an irradiation cycle of the irradiation light, a receiver that receives reflected light from the material to output as a pulse signal and receives disturbance light to output as a noise signal, an integrator that samples N pulse signals during a predetermined period and integrates the sampled N pulse signals to obtain a first integrated value, and samples N noise signals during a same period as the predetermined period with a same cycle as the irradiation cycle and integrates the sampled N noise signals to obtain a second integrated value, and an extractor that deducts the second integrated value from the first integrated value to extract an amount of the reflected light.

7 Claims, 9 Drawing Sheets (51) Int. Cl.
*G01J 3/10* (2006.01)
*G01J 3/42* (2006.01)
*G01N 21/359* (2014.01)
*G01N 21/3554* (2014.01)
*G01J 3/02* (2006.01)
*G01N 21/47* (2006.01)

(52) U.S. Cl.
CPC .............. *G01J 3/42* (2013.01); *G01N 21/314* (2013.01); *G01N 21/3554* (2013.01); *G01N 21/4738* (2013.01); *G01N 2021/3148* (2013.01); *G01N 2021/3155* (2013.01); *G01N 2021/3166* (2013.01); *G01N 2021/3181* (2013.01); *G01N 2021/4769* (2013.01); *G01N 2201/0627* (2013.01)

(58) Field of Classification Search
CPC ... G01N 2021/3166; G01N 2021/3181; G01N 2021/4769; G01N 21/314; G01N 21/3554; G01N 21/359; G01N 21/4738; G01N 2201/0627
See application file for complete search history.

(56) References Cited

U.S. PATENT DOCUMENTS

| | | | |
|---|---|---|---|
| 5,348,002 A | * | 9/1994 | Caro .................... A61B 5/0095 356/39 |
| 6,845,326 B1 | | 1/2005 | Panigrahi et al. |
| 2010/0053628 A1 | | 3/2010 | Kumagai et al. |
| 2012/0298847 A1 | | 11/2012 | Hayashi et al. |

OTHER PUBLICATIONS

Anonymous: "Nutrient-Wikipedia, the free encyclopedia", (Feb. 9, 2013), 4 pages.

T. Kojima et al., "Variety Discrimination and Qualitative Analysis of Protein in Barley by Near Infrared Spectroscopy." Bull. Fac. Agr., Saga Univ., vol. 78, pp. 1-9, 1995.

Extended European Search Report dated Apr. 14, 2016 for European Application No. 15200293.7.

* cited by examiner

MATERIAL ANALYTICAL SENSOR AND MATERIAL ANALYZER

CROSS-REFERENCE TO RELATED APPLICATION

The present application is based on and claims priority to Japanese patent application No. 2014-253795, filed Dec. 16, 2014, the disclosure of which is hereby incorporated by reference herein in its entirety.

BACKGROUND

Technical Field

The present invention relates to a material analytical sensor and a material analyzer capable of optically detecting a component contained in a material.

Description of Related Art

Conventionally, a material analytical sensor and a material analyzer capable of optically detecting a component contained in a material (sample) have been known by for example, "Variety Discrimination and Qualitative Analysis of Protein in Barley by Near Infrared Spectroscopy", Bull. Fac. Agr., Saga Univ. 78:1-9 (1995) (Non-Patent Document 1). A technique taught by Non-Patent Document 1 uses a near infrared spectroscopy analyzer for optically detecting protein contained in wheat as a material (sample).

The sensor and analyzer taught by Non-Patent Document 1 are configured to irradiate the material (sample) with near infrared light at a wavelength of 1100 to 2500 nm, and detect reflected light at 2 nm-wavelength intervals, so as to thereby measure a spectral distribution (raw spectral distribution) of the reflected light from the material (sample).

In order to eliminate effects of reflected and scattered light from the sample surface and identify a position of an absorption band of a wavelength of light absorbed by a component, a secondary spectrum distribution is obtained by secondary-diffracting the raw spectral distribution. The component contained in the material is quantitatively analyzed based on the wavelength region of the absorption band of the light of the secondary spectrum distribution.

SUMMARY

However, the conventional material analyzer is configured to disperse the reflected light from the surface of the material with the spectroscopic analyzer, and obtain an absorption spectrum with respect to each wavelength. Such a configuration complicates the analysis process, and makes it difficult to precisely estimate the amount of component contained in the material.

The present invention has been made in view of the above circumstances, and an object of the present invention is to provide a material analytical sensor and a material analyzer capable of easily and precisely estimating the amount of component contained in a material.

To achieve the above object, an aspect of the present invention provide a material analytical sensor including: an emitter that periodically irradiates a material with irradiation light including a wavelength region related to estimation of an amount of a component of the material; a controller that controls an irradiation cycle of the irradiation light; a receiver that receives reflected light from the material to output as a pulse signal and receives disturbance light during the irradiation cycle to output as a noise signal; an integrator that samples N pulse signals during a predetermined period in synchronization with the irradiation cycle and integrates the sampled N pulse signals to obtain a first integrated value, and samples N noise signals during a same period as the predetermined period with a same cycle as the irradiation cycle and integrates the sampled N noise signals to obtain a second integrated value; and an extractor that deducts the second integrated value from the first integrated value to extract an amount of the reflected light, wherein the irradiation light includes light in a first wavelength region, light in a second wavelength region, and light in a third wavelength region, the light being related to the estimation of the amount of the component of the material, the integrator obtains the first integrated value and the second integrated value corresponding to the first integrated value for the light in each of the first to the third wavelength regions, and the extractor deducts the second integrated value corresponding to the first integrated value from the first integrated value to extract the amount of reflected light for the light in each of the first to the third wavelength regions.

BRIEF DESCRIPTION OF DRAWINGS

FIGS. 5A and 5B are views schematically showing one example of integration of the reflected light shown in FIGS. 1, 3, and 4.

DETAILED DESCRIPTION

Hereinafter, a material analytical sensor and a material analyzer according to embodiments of the present invention will be described with reference to the drawings.

Embodiment 1

Figure 1:
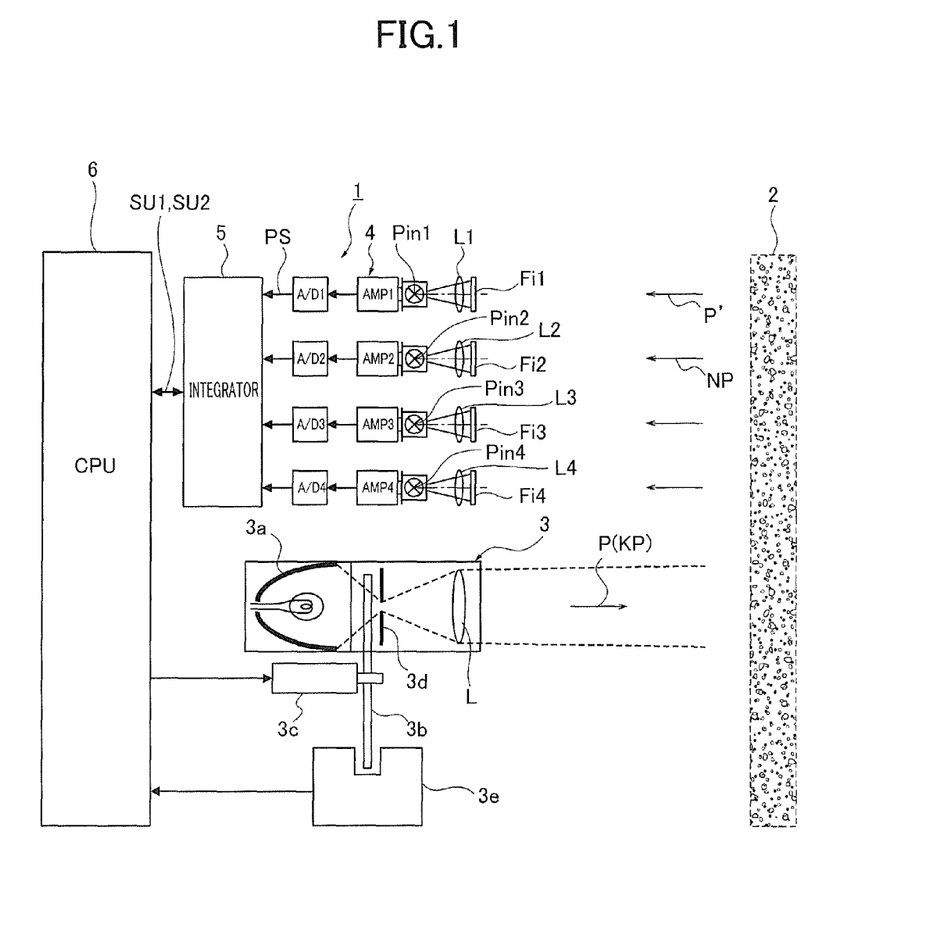
FIG. 1 is a block diagram showing a schematic configuration of a material analytical sensor according to Embodiment 1 of the present invention.
Figure 2:
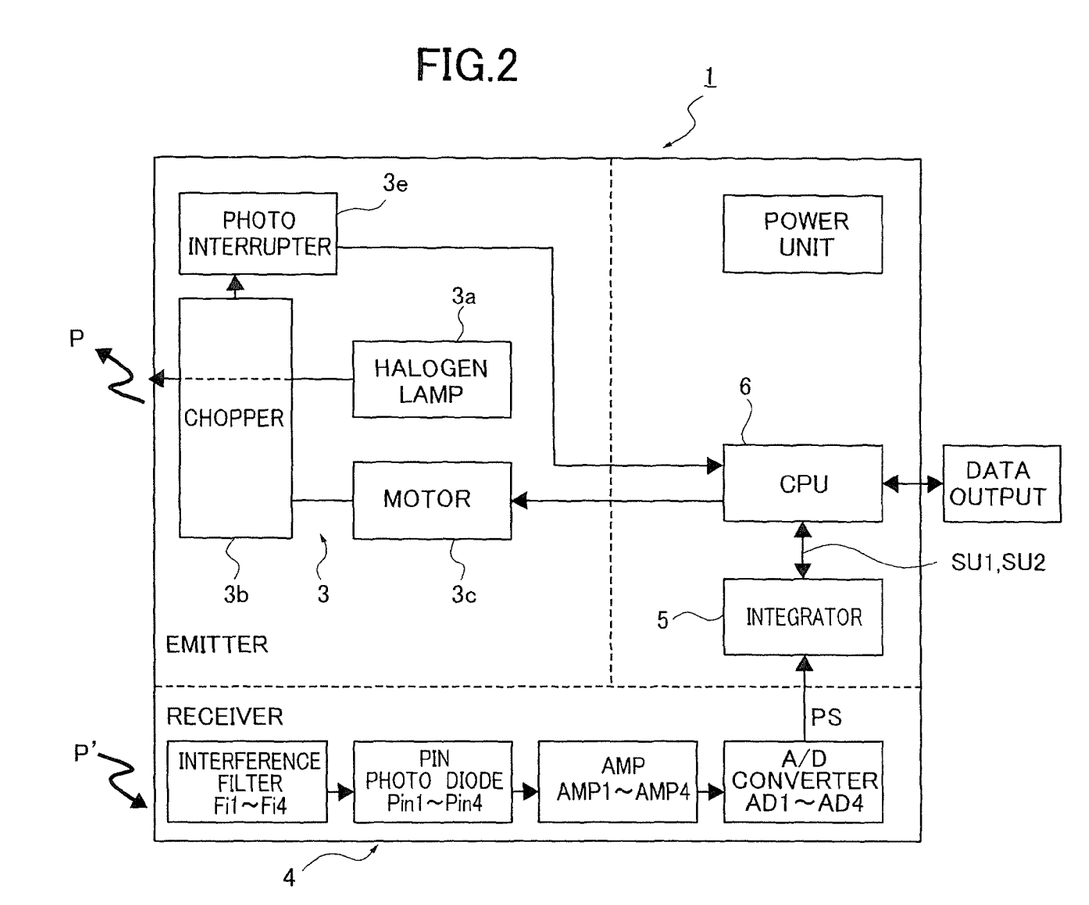
FIG. 2 a block diagram showing a circuit of the material analytical sensor shown in FIG. 1.

FIGS. 1 to 5 are views describing the material analytical sensor according to Embodiment 1. FIG. 1 is a block diagram showing the material analytical sensor according to Embodiment 1 of the present invention, and FIG. 2 is a block diagram showing a circuit of the material analytical sensor according to Embodiment 1 of the present invention.

In FIGS. 1 and 2, reference number 1 denotes a material analytical sensor and in FIG. 1, reference number 2 denotes a material as an analysis target. In this case, the material 2 as the analysis target is wheat, and protein as a component contained in the wheat is quantitatively analyzed. The material analytical sensor 1 includes a CPU 6, emitter 3, receiver 4, and integrator 5.

The emitter 3 irradiates the material 2 with irradiation light P including light in a first to fourth wavelength regions $\lambda 1$ to $\lambda 4$ related to the estimation of the component of the material 2. The light in the first to third wavelength regions $\lambda 1$ to $\lambda 3$ is pulse light KP related to the estimation of the amount of protein and the light in the fourth wavelength region $\lambda 4$ is pulse light KP in an absorption wavelength band of moisture related to the estimation of the amount of protein. The emitter 3 periodically irradiates the material 2 with the irradiation light P.

Figure 3:
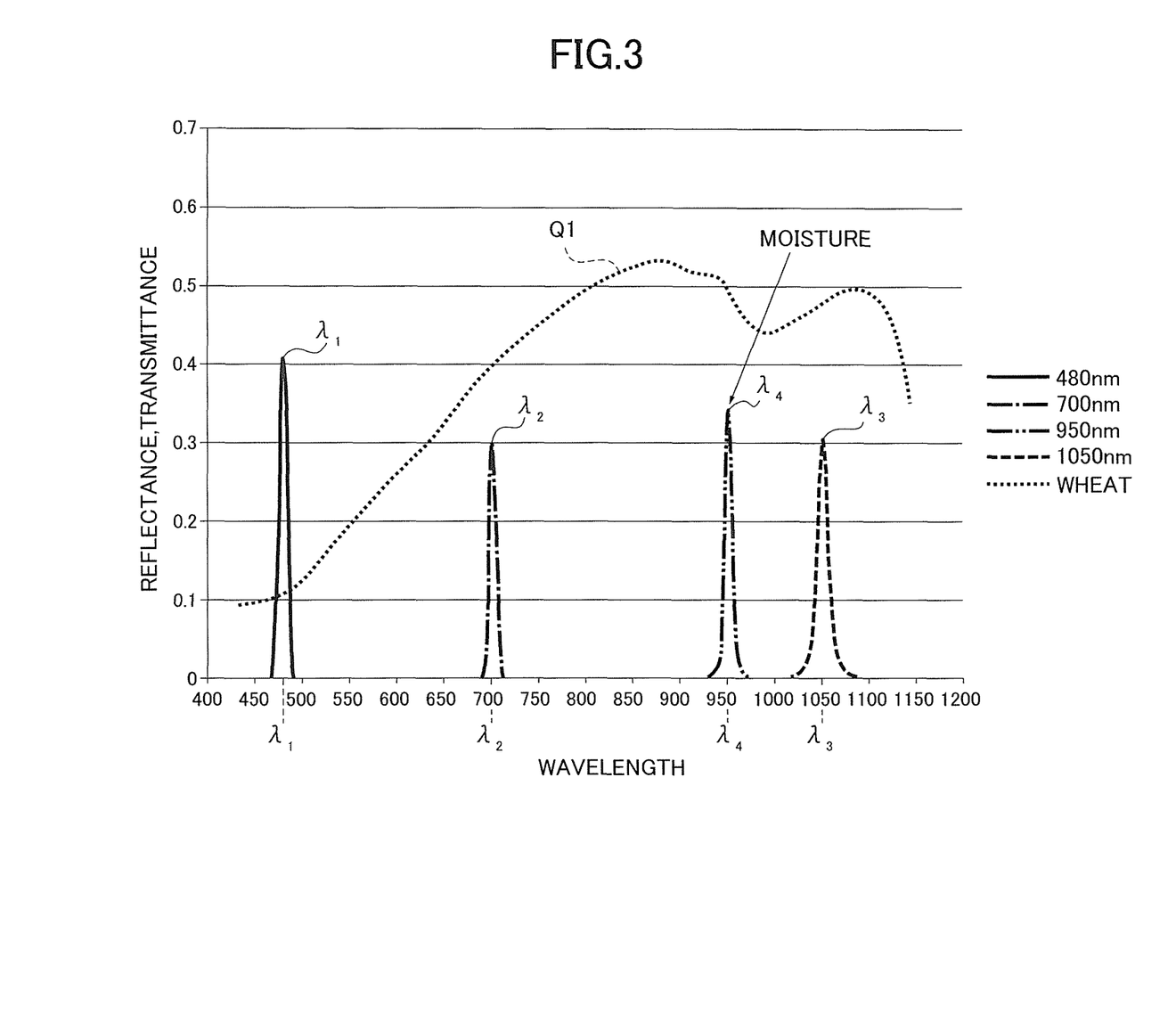
FIG. 3 is a graph showing a relationship between a spectral distribution curve related to estimation of the amount of protein as a component contained in the material shown in FIG. 1 and wavelength regions related to the estimation of the amount of protein.

As shown in FIG. 3, the irradiation light P includes visible light in the first wavelength region $\lambda 1$, near infrared light in the second wavelength region $\lambda 2$, near infrared light in the third wavelength region $\lambda 3$ different from the second wavelength region $\lambda 2$, and near infrared light in the fourth wavelength region $\lambda 4$.

The first wavelength region $\lambda 1$ has the central wavelength of about 480 nm, the second wavelength region $\lambda 2$ has the central wavelength of about 700 nm, the third wavelength region $\lambda 3$ has the central wavelength of about 1050 nm, and the fourth wavelength region $\lambda 4$ has the central wavelength of about 950 nm.

A spectral distribution curve Q1 changes in accordance with the amount of protein and moisture contained in the wheat. The first to fourth wavelength regions $\lambda 1$ to $\lambda 4$ are determined by obtaining much data of the spectral distribution curve Q1 and applying PLS regression analysis to the data.

Next, a calibration curve is created by multiple regression analysis with a true value of the amount of protein (the value of the amount of protein obtained by an analysis method for use in known quantitative analysis of protein) and the first to fourth wavelength regions $\lambda 1$ to $\lambda 4$ determined with the material analytical sensor 1 according to Embodiment 1, and an estimation coefficient on the protein is determined. In FIG. 3, the horizontal axis represents a wavelength and the vertical axis represents reflectance or transmittance.

A calibration curve is also created by multiple regression analysis with a true value of the amount of moisture (the value of the amount of moisture obtained by an analysis method for use in known quantitative analysis of moisture) and the first to fourth wavelength regions $\lambda 1$ to $\lambda 4$ determined with the material analytical sensor 1 according to Embodiment 1, and an estimation coefficient on the amount of moisture is determined.

Since the wavelength mainly affected by the amount of moisture is a wavelength region near the fourth wavelength region $\lambda 4$ of 950 nm, the fourth wavelength region $\lambda 4$ is weighted, and the estimation coefficient on the amount of moisture is determined by using all of the first to the fourth wavelength regions $\lambda 1$ to $\lambda 4$.

As shown in FIGS. 1 and 2, the emitter 3 includes a light source 3a that emits the irradiation light P including the visible light in the first wavelength region $\lambda 1$, the near infrared light in the second wavelength region $\lambda 2$, the near infrared light in the third wavelength region $\lambda 3$, and the near infrared light in the fourth wavelength region $\lambda 4$, a chopper 3b that irradiates the material 2 with the irradiation light P as the pulse light KP, and a condenser lens L that condenses the irradiation light P to be emitted as parallel light flux. The chopper 3b is driven by a motor 3c. A halogen lamp that generates light in a wavelength region $\lambda$ including the wavelength region $\lambda 1$ of the visible light and the wavelength regions $\lambda 2$ to $\lambda 4$ of the near infrared light is used for the light source 3a.

The chopper 3b includes in the circumference thereof slits (not shown) at predetermined intervals. The chopper 3b is disposed in front of the opening of an aperture member 3d. The chopper 3b is provided with a photo interrupter 3e facing the slits. The photo interrupter 3e is used to detect a light-emitting pulse.

The CPU 6 controls the rotation of the motor 3c such that the rotation cycle of the chopper 3b becomes constant based on the pulses detected by the photo interrupter 3e. The material 2 is thereby irradiated with the irradiation light P shown in (B) of FIG. 4 with an irradiation cycle T1 shown in (A) of FIG. 4.

Figure 4:
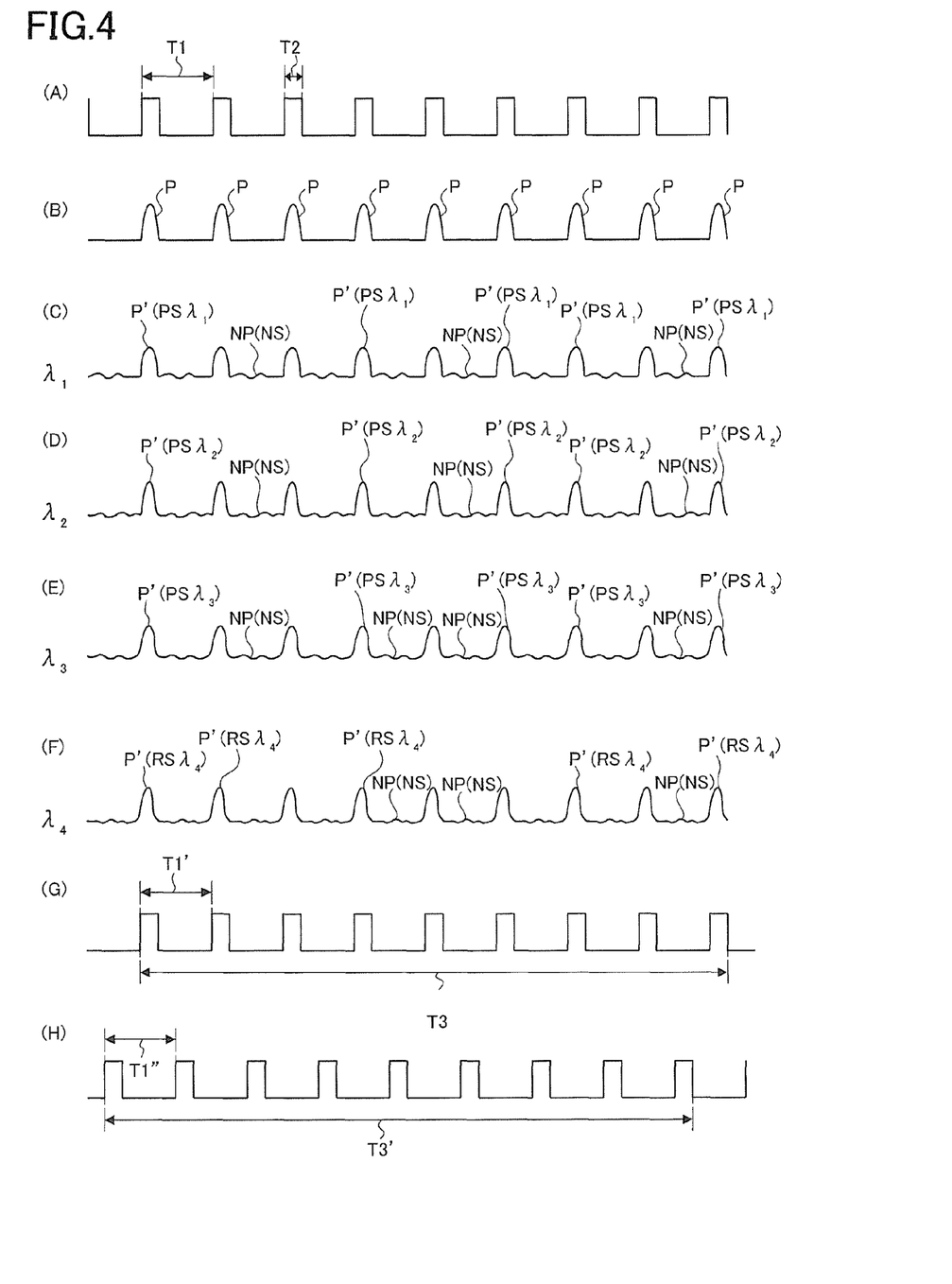
FIG. 4 is a view showing a relationship among irradiation timing of irradiation light emitted from an emitter shown in FIG. 1, pulse light, reflected light from a material, disturbance light, and sampling timing between the reflected light and the disturbance light.

The CPU 6 operates as a controller that controls the irradiation cycle T1 of the irradiation light P to be constant in corporation with the photo interrupter 3e. In FIG. 4 (A), reference number T2 represents an irradiation pulse width of the irradiation light P.

The receiver 4 includes a filter (interference filter) Fi1 that transmits the visible light in the first wavelength region $\lambda 1$, filters (interference filters) Fi2 to Fi4 that transmit the near infrared light in the second to fourth wavelength regions $\lambda 2$ to $\lambda 4$, respectively, condenser lenses L1 to L4 that condense the light transmitted through the filters Fi1 to Fi4, respectively, and light-receiving elements Pin1 to Pin4 arranged in accordance with the filters and the lenses. These light-receiving elements Pin1 to Pin4 are made up of for example, PIN photodiodes, respectively.

Each of the light-receiving elements Pin1 to Pin4 receives the light including reflected light P' reflected by the material 2 to output a pulse signal PS, and receives the light in each wavelength region in disturbance light NP from the material 2 during the irradiation cycle T1 to output a noise signal NS.

FIG. 4 shows in (C) to (F) the reflected light P' and the pulse signals PS$\lambda 1$ to PS$\lambda 4$ corresponding to the respective first to fourth wavelength regions $\lambda 1$ to $\lambda 4$ along with the noise light NP and the noise signals NS.

As shown in FIG. 1, the output of each of the light-receiving elements Pin1 to Pin4 is amplified by each of amplifiers AMP1 to AMP4, the amplified output is converted into digital data by each of A/D convertors A/D1 to A/D4, and the digital data is input to the integrator (FPGA integration) 5.

The pulse signals PS$\lambda 1$ to PS$\lambda 4$ in the first to fourth wavelength regions $\lambda 1$ to $\lambda 4$ are simultaneously input to the integrator 5. The integrator 5 obtains a first integrated value SU1 for each of the pulse signals PS$\lambda 1$ to PS$\lambda 4$ based on the control of the CUP. The first integrated value SU1 is obtained by sampling N pulse signals for each of the pulse signals PS$\lambda 1$ to PS$\lambda 4$ in chronological order during a predetermined period T3 with the same sampling cycle T1' as the irradiation cycle T1 in synchronization with the irradiation cycle T1, as shown in (G) of FIG. 4, and integrating the sampled N pulse signals for each of the pulse signals PS$\lambda 1$ to PS$\lambda 4$. The calculation example of the first integrated value SU1 will be described later. Reference number N represents a positive integer.

Similarly, the integrator 5 obtains a second integrated value SU2 corresponding to the first integrated value SU1 based on the control of the CPU 6. The second integrated value SU2 is obtained by sampling N noise signals for each of the noise signals NS during the same predetermined period T3' as the predetermined period T3 with the same sampling cycle T1" as the irradiation cycle T1, as shown in (H) of FIG. 4, and integrating the sampled N noise signals for each of the noise signals NS.

FIG. 4 shows in (G) the sampling cycle T1' and the predetermined period T3 as the sampling period for each of the pulse signals PSλ1 to PSλ4. FIG. 4 shows in (H) the sampling cycle T1" and the predetermined period T3' as the sampling period for each of the noise signals NS.

One example of the integration of the first integrated value SU1 is described below. The integrator 5 obtains the maximum value of the reflected light P' (pulse signal PS (PSλ1 to PSλ4)) with the irradiation cycle T1 by equally dividing the irradiation pulse width T2 based on the control of the CPU 6.

Figure 5A:
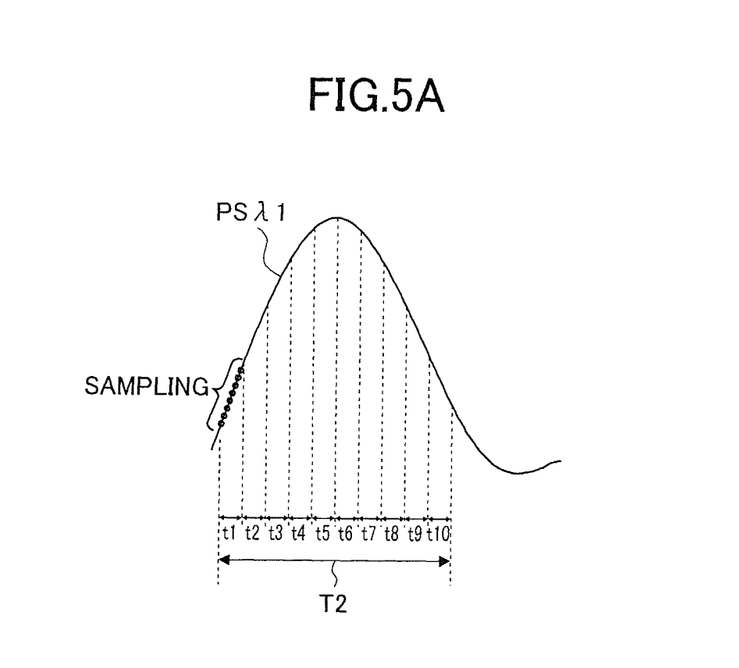
FIG. 5A is a view conceptually showing a sampling state of data of each divided interval obtained by dividing the pulse width of the reflected light into 10.
Figure 5B:
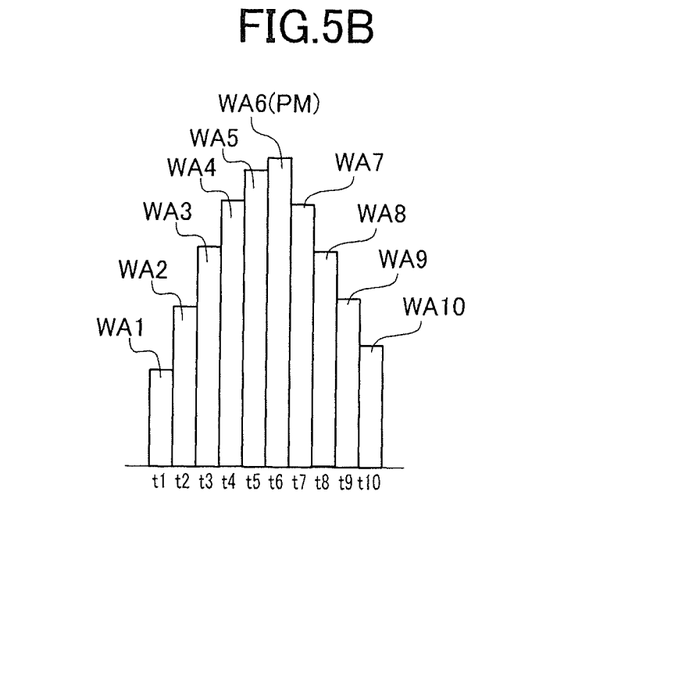
FIG. 5B is view conceptually showing a process of obtaining the maximum value based on the integration of the sampling data of each divided interval (WA1, WA2, . . . , WA10)

As shown in FIG. 5A, for example, the data of the pulse signal PSλ1 is divided into 10. The data in each interval of the divided pulse signal PSλ1 is segmented into 8, and the data in each segmented interval is sampled to obtain each of added values WA1 to WA10, as shown in FIG. 5B.

Next, the integrator 5 compares the added values WA1 to WA10 to obtain the maximum value PM of the pulse signal PSλ1 based on the control of the CPU 6. The maximum value PM is obtained for the N pulse signals for each of the pulse signals PSλ1 to PSλ4 sampled during the predetermined period T3.

The first integrated value SU1 corresponding to each of the first to fourth wavelength regions λ1 to λ4 is thereby obtained. The second integrated value SU2 is similarly obtained for each of the noise signals NA. In FIGS. 5A and 5B, the pulse signal PSλ1 and the added values WA1 to WA10 are processed by analogue calculation for convenience in description, but they can be processed by digital calculation.

The CPU 6 deducts the second integrated value SU2 corresponding to the first integrated value SU1 from the first integrated value SU1 obtained for each of the first to fourth wavelength regions λ1 to λ4 to extract the amount of reflected light for the pulse light KP in each of the first to fourth wavelength regions λ1 to λ4. Namely, the CPU 6 operates as an extractor that deducts the second integrated value SU2 from the first integrated value SU1 to extract the amount of reflected pulse light KP.

Next, the CPU 6 estimates the amount of protein based on the measured value in which the second integrated value SU2 is deducted from the first integrated value SU1 and the estimated coefficient obtained by the multiple regression analysis. In addition, the data of the amount of reflected light and the detection results are output outside via an input and output interface as appropriate.

According to Embodiment 1, since the disturbance light NP contained in the reflected light P' of the pulse light KP can be eliminated, the detection accuracy of the amount of reflected light P' is improved, and thus, the estimation accuracy of the amount of protein is improved.

Embodiment 2

Figure 6:
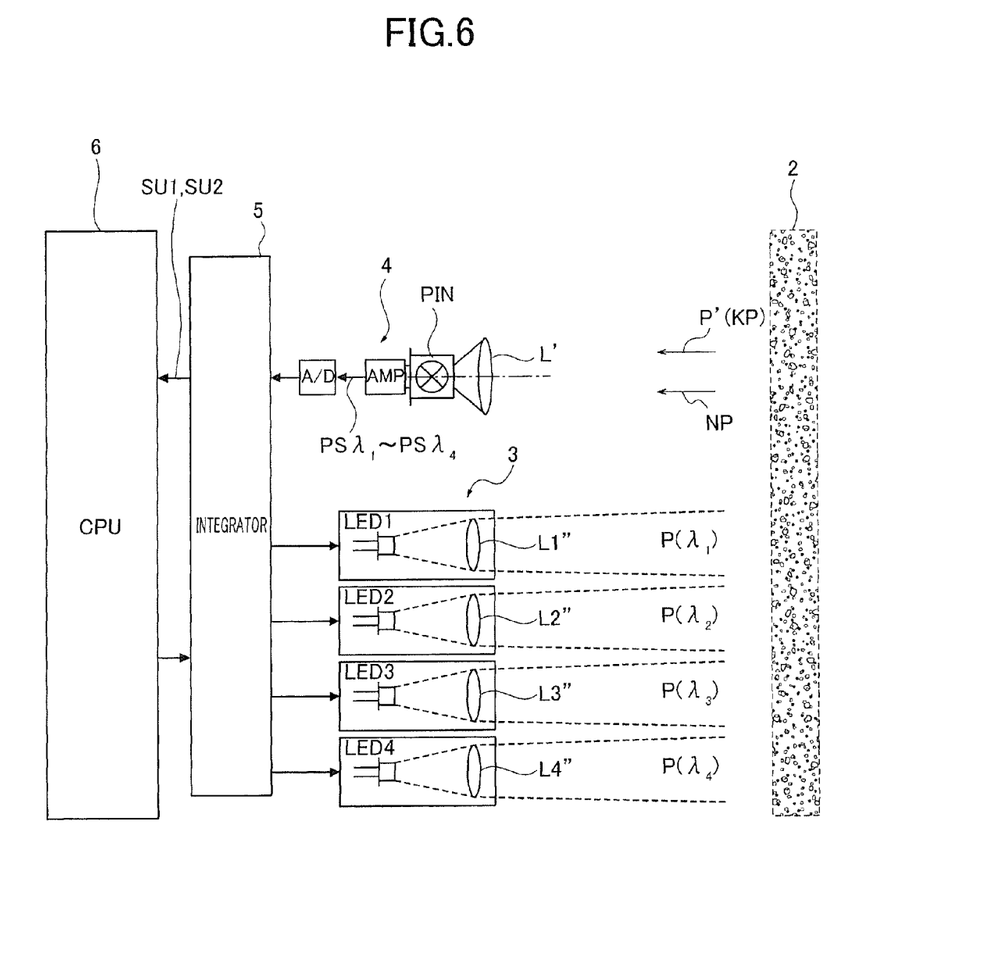
FIG. 6 is a block diagram showing a schematic configuration of a material analytical sensor according to Embodiment 2 of the present invention.
Figure 7:
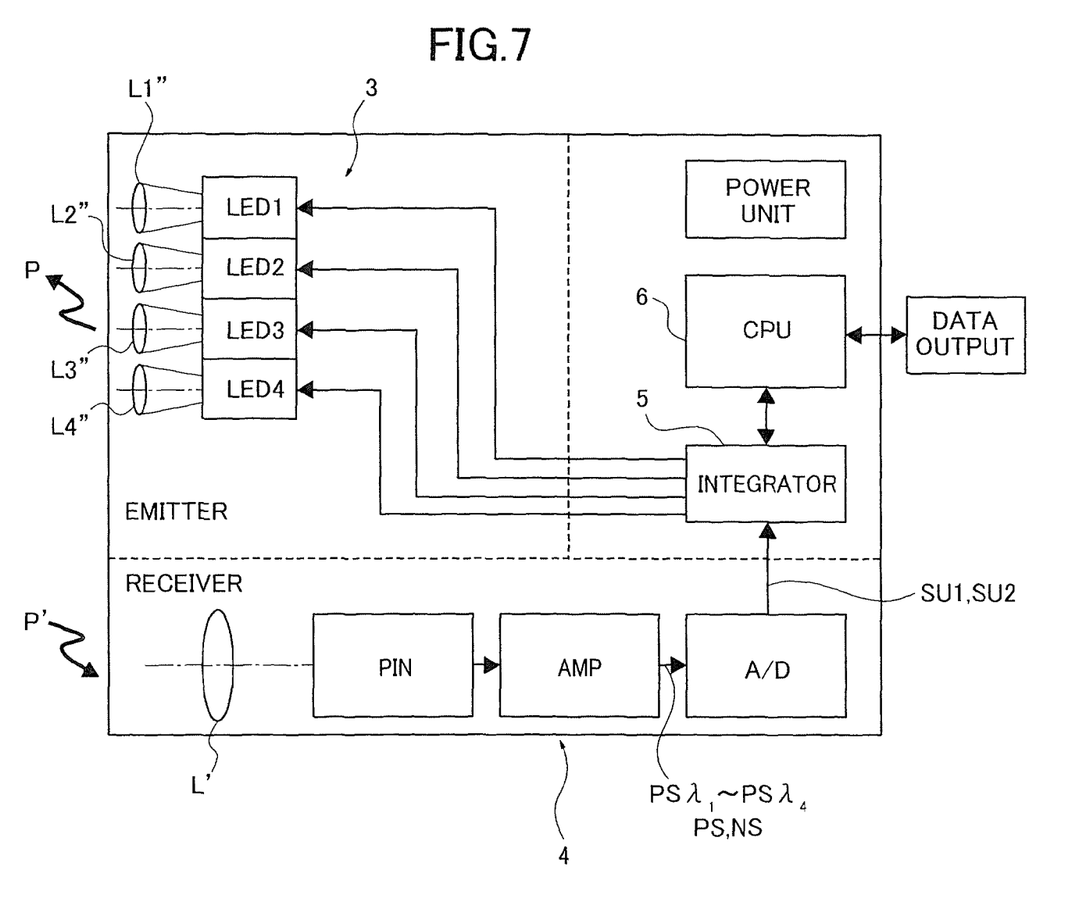
FIG. 7 is a block diagram showing a circuit of the material analytical sensor shown in FIG. 6.

In Embodiment 2, as shown in FIGS. 6 and 7, an emitter 3 includes a first light-emitting diode LED1 that emits visible light in a first wavelength region λ1, second and third light-emitting diodes LED2 and LED3 that emit near infrared light in second and third wavelength regions λ2 and λ3, respectively, and a fourth light-emitting diode LED4 that emits near infrared light in a fourth wavelength region λ4.

The emitter 3 includes condenser lenses L1" to L4" that condense light from the first to fourth light-emitting diodes LED1 to LED4 to irradiate a material 2 with parallel light flux, respectively.

Figure 8:
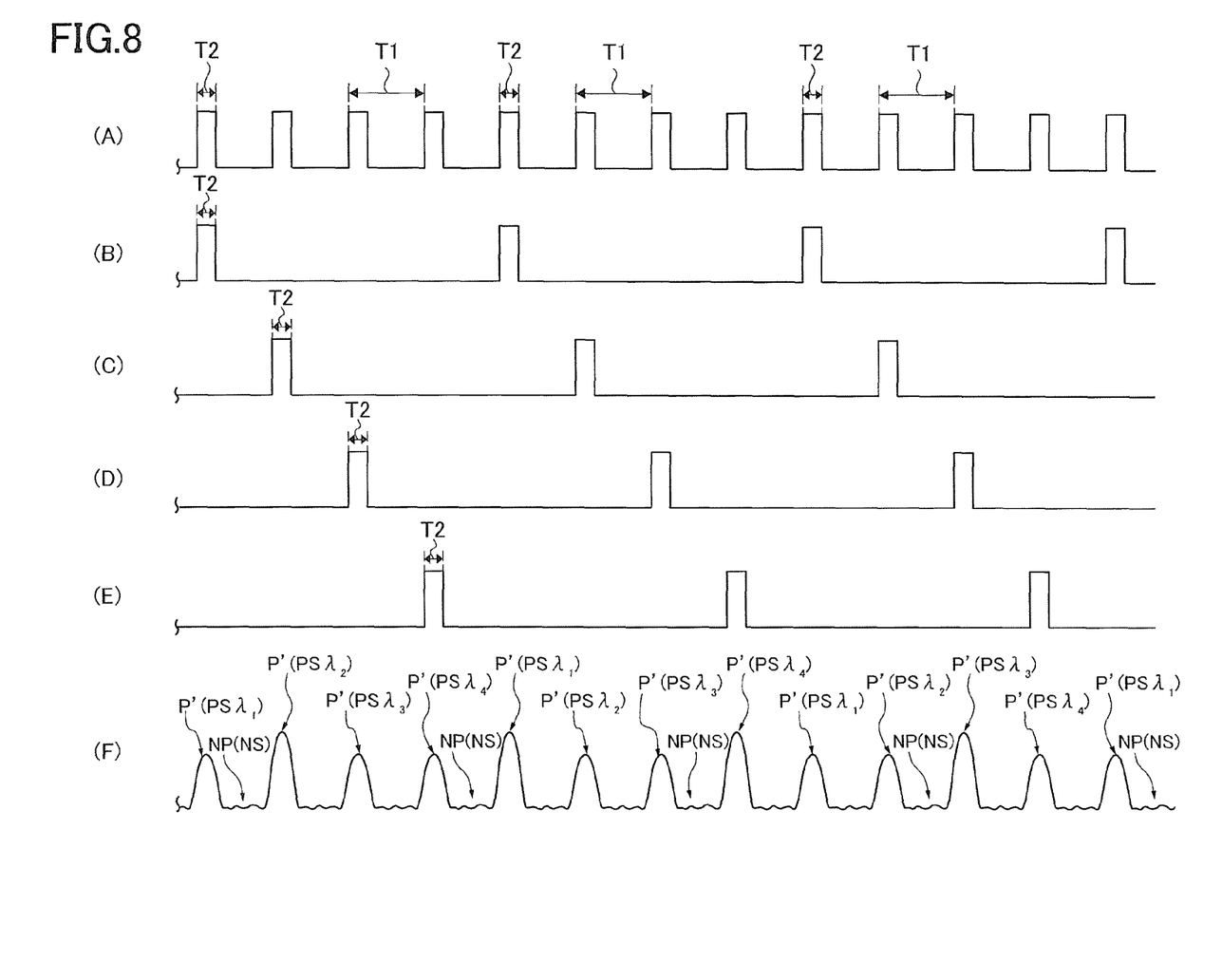
FIG. 8 is a view showing a relationship among irradiation timing of irradiation light emitted from an emitter shown in FIG. 7, pulse light, reflected light from a material, disturbance light, and a sampling timing between the reflected light and the disturbance light.

The CPU 6 controls the emission of the light-emitting diodes LED1 to LED4 to irradiate the material 2 with irradiation light P with an irradiation cycle T1 similar to Embodiment 1, as shown in (A) of FIG. 8, and also to irradiate the material 2 with the visible light in the first wavelength region λ1 and the near infrared light in the second to fourth wavelength regions λ2 to λ4 in chronological order in different timing with the irradiation cycle T1, as shown in (B) to (E) of FIG. 8.

In Embodiment 2, as shown in (B) to (E) of FIG. 8, the irradiation cycle of the light in each of the first to fourth wavelength regions λ1 to λ4 is four times the irradiation cycle T1 of the irradiation light P shown in (A) of FIG. 8. In Embodiment 2, an integrator 5 operates as a controller that controls the emission of the first to fourth light-emitting diodes LED1 to LED4 in corporation with the CPU 6.

A receiver 4 includes a condenser lens L' that condenses the light from the material 2 and a pin photodiode as a light-receiving element PIN, as shown in FIGS. 6 and 7. The output from the pin photodiode is amplified by an amplifier AMP, converted into digital signals by an A/D convertor, and input to the integrator 5 as data in chronological order.

As shown in (F) of FIG. 8, the receiver 4 receives the reflected light P' from the material 2 as the pulse light KP irradiated with the irradiation cycle T1 shown in (A) of FIG. 8 in chronological order, and also receives the disturbance light NP during the irradiation cycle T1. Namely, similar to Embodiment 1, the receiver 4 only receives the disturbance light NP during the irradiation cycle T1.

FIG. 8 shows in (F) the reflected light P' corresponding to the first wavelength region λ1 and its pulse signal PSλ1, the reflected light P' corresponding to the second wavelength region λ2 and its pulse signal PSλ2, the reflected light P' corresponding to the third wavelength region λ3 and its pulse signal PSλ3, the reflected light P' corresponding to the fourth wavelength region λ4 and its pulse signal PSλ4, the noise light NP, and the noise signals NS.

The integrator 5 obtains a first integrated value SU1 based on the control of the CPU 6. The first integrated value SU1 is obtained by sampling N pulse signals PS for each of the pulse signals PS in the first to fourth wavelength regions λ1 to λ4 during a predetermined period T3 in synchronization with the irradiation cycle T1 of the irradiation light P, and integrating the sampled N pulse signals PS.

Similarly, the integrator 5 obtains a second integrated value SU2 based on the control of the CPU 6. The second integrated value SU2 is obtained by sampling N noise signals NS corresponding to each of the pulse signals PS in the first to fourth wavelength regions λ1 to λ4 during the same period as the predetermined period T3 in synchronization with the irradiation cycle T1 of the irradiation light P, and integrating the sampled N noise signals.

Namely, the number N of pulse signals PS that is integrated for obtaining the first integrated value SU1 is the same for each of the pulse signals PS in the first to fourth wavelength regions λ1 to λ4. The number N of the noise signals NS that is integrated for obtaining the second integrated value SU2 corresponding to the first integrated value SU1 is also the same as the number N of the pulse signals PS that is integrated for each of the first to fourth wavelength regions λ1 to λ4.

In Embodiment 2, since the integration process with the integrator 5 is the same as that in Embodiment 1 except that the emission timing of the pulse light KP differs, the sampling cycle of the pulse signal PS is 4 times that in Embodiment 1, and the sampling period T3 is 4 times that in Embodiment 1, the detailed description thereof will be omitted.

In Embodiment 2, since the disturbance light NP contained in the reflected light P' of the pulse light KP can be eliminated similar to Embodiment 1, the detection accuracy of the amount of reflected light P' can be improved. Although, in the above embodiments, the estimation of the amount of protein which is an organic material is described, the present invention is not limited thereto. The present invention can be used for estimation of the amount of component of an inorganic material.

Embodiment 3

Figure 9:
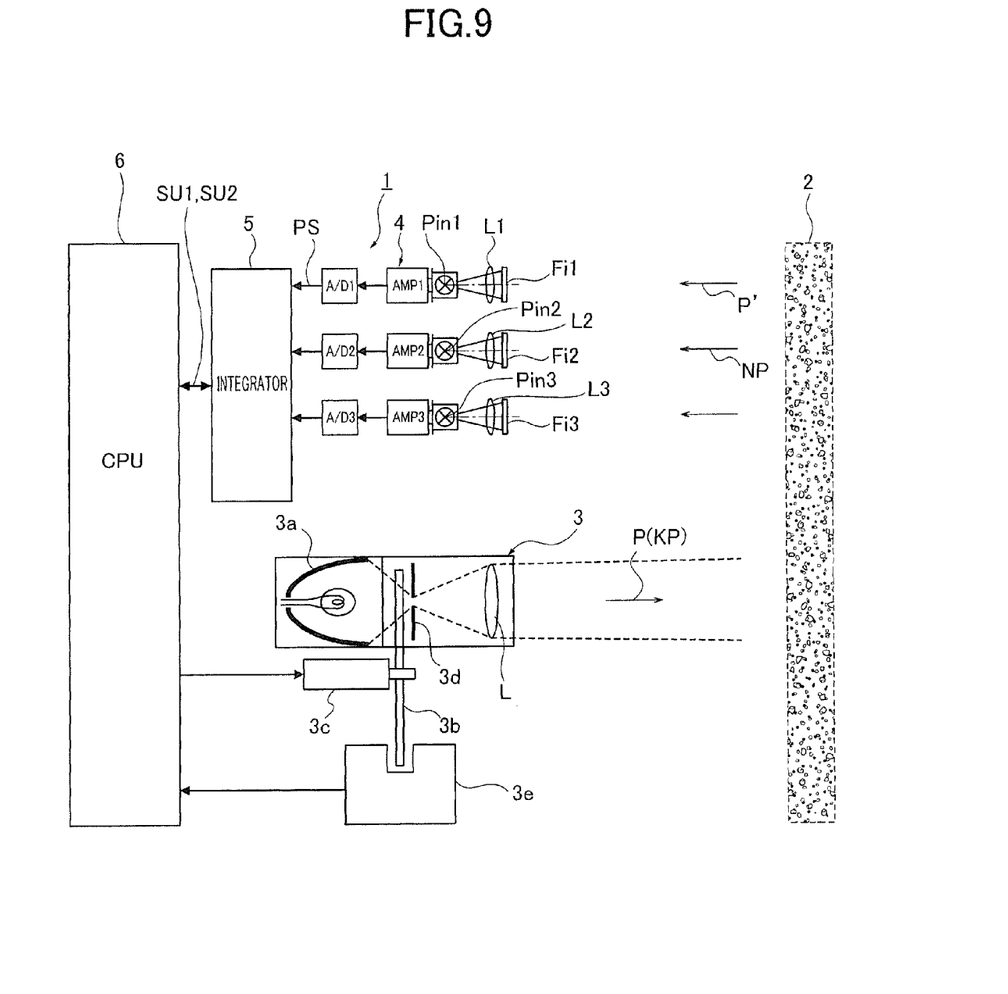
FIG. 9 is a block diagram showing a schematic configuration of a material analytical sensor according to Embodiment 3 of the present invention.

FIG. 9 is a block diagram showing a schematic configuration of a material analytical sensor according to Embodiment 3 of the present invention. The material analytical sensor according to Embodiment 3 does not use the fourth wavelength region $\lambda 4$ mainly affected by the amount of moisture.

The material analytical sensor according to Embodiment 3 uses the first to third wavelength regions $\lambda 1$ to $\lambda 1$ related to the estimation of the component of the material 2. The configuration of an emitter 3 in this embodiment is similar to that in Embodiment 1. Similar to Embodiment 1, the emitter 3 irradiates the material 2 with the irradiation light P including at least the light in the first to third wavelength regions $\lambda 1$ to $\lambda 3$ related to the estimation of the component of the material 2 as the pulse light KP. The pulse light KP relates to the estimation of the amount of protein. Similar to Embodiment 1, the first wavelength region $\lambda 1$ has the central wavelength of about 480 nm, the second wavelength region $\lambda 2$ has the central wavelength of about 700 nm, and the third wavelength region $\lambda 3$ has the central wavelength of about 1050 nm.

A receiver 4 includes a filter (interference filter) Fi1 that transmits the visible light in the first wavelength region $\lambda 1$, the filters (interference filter) Fi2 and Fi3 that transmit the near infrared light in the second and third wavelength regions $\lambda 2$ and $\lambda 3$, respectively, condenser lenses L1 to L3 that condense the light transmitted through the filters Fi1 to Fi3, respectively, and light-receiving elements Pin1 to Pin3 arranged corresponding to these filters and lenses. These light-receiving elements Pin1 to Pin3 are made up of for example, PIN photodiodes, respectively.

A spectral distribution curve Q1 (refer to FIG. 3) changes in accordance with the amount of protein and moisture contained in the wheat as the material 2. However, the first to third wavelength regions $\lambda 1$ to $\lambda 3$ can be determined without determining the estimation coefficient on the amount of moisture. To determine the first to third wavelength regions $\lambda 1$ to $\lambda 3$, much more data of the spectral distribution curve Q1 is obtained than Embodiments 1 and 2, and PLS regression analysis is applied to the data.

Next, a calibration curve is created by multiple regression analysis with a true value of the amount of protein (the value of the amount of protein obtained by an analysis method for use in known quantitative analysis of protein) and the first to third wavelength regions $\lambda 1$ to $\lambda 3$ determined with the material analytical sensor 1 according to Embodiment 3, and an estimation coefficient on the protein is determined.

By using the estimation coefficient on the protein, the estimation value of the amount of protein can be obtained with the same method as in Embodiments 1 and 2. According to Embodiment 3, the material can be analyzed without using the amount of moisture.

Modified Example

In Embodiment 3, the material analytical sensor shown in FIG. 9 is achieved without using the filter (interference filter) Fi4 that transmits the infrared light in the fourth wavelength region $\lambda 4$, the light-receiving element Pin4, the amplifier AMP4, and the A/D convertor A/D4 in the receiver 4 shown in FIG. 1.

However, by removing the fourth light-emitting diode LED 4 that emits the near infrared light in the fourth wavelength region $\lambda 4$ shown in FIG. 6, a calibration curve is created by the multiple regression analysis with the first to third wavelength regions $\lambda 1$ to $\lambda 3$ determined with the material analytical sensor 1 according to this example with a configuration, and the estimation coefficient on the protein is thereby determined.

According to the embodiments of the present invention, the amount of component contained in the material can be precisely estimated. The material analytical sensor can be downsized and the costs for the sensor can be also reduced. Although the present invention has been described in terms of exemplary embodiments, it is not limited thereto. It should be appreciated that variations or modifications may be made in the embodiments described by persons skilled in the art without departing from the scope of the present invention as defined by the following claims.

What is claimed is:

1. A material analytical sensor comprising:
an emitter that periodically irradiates a material with irradiation light including a wavelength region related to estimation of an amount of a component of the material;
a controller that controls an irradiation cycle of the irradiation light;
a receiver that receives reflected light from the material to output as a pulse signal and receives disturbance light during the irradiation cycle to output as a noise signal;
an integrator that samples N pulse signals during a predetermined period in synchronization with the irradiation cycle and integrates the sampled N pulse signals to obtain a first integrated value, and samples N noise signals during a same period as the predetermined period with a same cycle as the irradiation cycle and integrates the sampled N noise signals to obtain a second integrated value; and
an extractor that deducts the second integrated value from the first integrated value to extract an amount of the reflected light, wherein
the irradiation light includes light in a first wavelength region, light in a second wavelength region, and light in a third wavelength region, the light being related to the estimation of the amount of the component of the material,
the integrator obtains the first integrated value and the second integrated value corresponding to the first integrated value for the light in each of the first to the third wavelength regions, and
the extractor deducts the second integrated value corresponding to the first integrated value from the first integrated value to extract the amount of reflected light for the light in each of the first to the third wavelength regions; and wherein the emitter includes a first light-emitting diode that emits the light in the first wavelength region, a second light-emitting diode that emits the light in the second wavelength region, and a third light-emitting diode that emits the light in the third wavelength region, and the controller controls emission timing of the first to third light-emitting diodes to irradiate the material with the light in the first wavelength region, the light in the second wavelength region, and the light in the third wavelength region in chronological order in different timing with the irradiation cycle.

2. The material analytical sensor as claimed in claim 1, wherein the irradiation light includes light in a fourth wavelength region, and the extractor extracts an amount of reflected light corresponding to the light in the fourth wavelength region.

3. A material analyzer comprising:

the material analytical sensor as claimed in claim 2, wherein the light in the first to third wavelength regions relates to the estimation of the amount of protein as the component of the material, the light in the first wavelength region is visible light, the light in the second wavelength region and the light in the third wavelength regions are near infrared light having a different wavelength region, and the light in the fourth wavelength region is near infrared light in an absorption wavelength band of moisture.

4. The material analytical sensor as claimed in claim 1, wherein the emitter includes a light source that emits the irradiation light including the light in the first to third wavelength regions, the emitter includes a condenser lens that condenses the irradiation light from the light source to be emitted as parallel light flux, and the receiver includes a condenser lens that condenses the light from the material.

5. The material analytical sensor as claimed in claim 1, wherein the emitter includes a condenser lens that condenses the light emitted from each of the light emitting diodes to irradiate the material with parallel light flux, and the receiver includes a condenser lens that condense the light from the material.

6. The material analytical sensor as claimed in claim 1, wherein the emitter includes a fourth light-emitting diode that emits light in a fourth wavelength region, and the controller controls the emission timing of the first to fourth light-emitting diodes to irradiate the material with the light in the first wavelength region, the light in the second wavelength region, the light in the third wavelength region, and the light in the fourth wavelength region in chronological order in different timing with the irradiation cycle.

7. A material analyzer comprising:

the material analytical sensor as claimed in claim 1, wherein the light in the first to third wavelength regions relates to the estimation of the amount of protein as the component of the material, the light in the first wavelength region is visible light, and the light in the second wavelength region and the light in the third wavelength region are near infrared light having a different wavelength region.

* * * * *